United States Patent [19]

Perrot

[11] 4,315,924

[45] Feb. 16, 1982

[54] NOVEL MEDICAMENT BASED ON ASPIRIN AND HEPTAMINOL

[75] Inventor: Jacques Perrot, Paris, France

[73] Assignee: Societe D'Etudes Scientifiques et Industrielles, Paris, France

[21] Appl. No.: 205,727

[22] Filed: Nov. 10, 1980

[30] Foreign Application Priority Data

Nov. 26, 1979 [FR] France .............................. 79 29036

[51] Int. Cl.$^3$ .................. A61K 31/60; A61K 31/605; A61K 31/615
[52] U.S. Cl. .................................. 424/233; 424/230; 424/235

[58] Field of Search ...................... 424/230, 235, 233

[56] References Cited

PUBLICATIONS

Chem. Abstracts, 9th Collective Index–Chem. Sub. G–Hexanol, p. 18241CS.

Primary Examiner—Stanley J. Friedman
Attorney, Agent, or Firm—Omri M. Behr

[57] ABSTRACT

The present invention concerns a novel medicament based on aspirin and heptaminol (that is to say, 6-amino-2-methyl-2-heptanol).

6 Claims, No Drawings

NOVEL MEDICAMENT BASED ON ASPIRIN AND HEPTAMINOL

Aspirin, or acetylsalicylic acid is usually employed as an analgesic; heptaminol, more particularly in its hydrochloride form, is essentially used as a cardiotonic, the stimulating effects of heptaminol on the cardiovascular system permitting that compound to serve as an agent for correcting cardiac deficiencies and certain hypotensions. The effects of aspirin and heptaminol are therefore separate.

It has been found that the aspirin-heptaminol association achieved surprising results which in every case are superior to those produced by aspirin alone or by heptaminol alone.

Thus, the analgesic effect on mice was studied with the aspirin-heptaminol association on the one hand, and with aspirin alone, on the other hand. This research was carried out orally using the phenylbenzoquinone test.

The analgesic activity of the aspirin-heptaminol association, in a ratio of $\frac{2}{3}-\frac{1}{3}$, was evaluated by the reduction, in the mouse which had been treated, in the number of 'wriggles' or 'squirming' movements caused by an intra-peritoneal injection of 2-phenyl 1,4-benzoquinone. Each experimental group comprised 15 randomly distributed animals of the NMRI-Han stock, about 5 weeks old and weighing between 20 and 22 grams. The whole of this study related to 75 male mice of which 10 were used as controls.

The test was used in accordance with the experimental methods decribed by H. BLUMBERG et Coll. (Proc. Soc. Exp. Biol. and Med. 1965, 118, 3, 763–766), that is to say, each motor manifestation is counted for 1 point and the total number of 'wriggles' of each animal is noted during the period of 20 minutes following the injection of phenylbenzoquinone. The 'control' value is determined from the mean number observed in the animals without treatment who were studied the same day; calculation of the analgesic activity is based on the percentage of animals which showed only less than 50 percent of the mean number of twisting motions of the group without treatment.

The analgesic dose 50 (AD 50) and its limits of reliance for $P=0.05$ are then determined using the graph method of J. T. LITCHFIELD and F. WILCOXON (J. Pharm. Exp. Ther. 1949, 96, 99–113). The results appear in the following tables:

| Doses mg/kg (orally) | Number of animals | Number of animals protected | % of animals protected |
|---|---|---|---|
| | | with regard to phenylbenzoquinone | |
| 18.57 | 15 | 3 | 20.0 |
| 37.5 | 15 | 6 | 40.0 |
| 75.0 | 15 | 8 | 53.3 |
| 150.0 | 15 | 12 | 80.0 |
| Analgesic dose 50 (AD 50) | | | 54.00 mg/kg |
| Lower limit | | | 34.74 mg/kg |
| Upper limit | | | 83.93 mg/kg |

The AD 50 of the association expressed in respect of aspirin is then 36 mg/kg with limits of reliance equal to 23.16 and 55.95 mg/kg.

It should be recalled that, under the same experimental conditions, the analgesic dose 50 (AD 50) of acetylsalicylic acid is equal to 145 mg/kg with limits of reliance of 91.1 and 230.8 mg/kg for $P=0.05$.

Comparison between the analgesic doses 50 of aspirin and the aspirin-heptaminol association gives a ratio equal to:

$$2.69 \left( \frac{AD\ 50\ \text{aspirin} = 145}{AD\ 50\ \text{aspirin-heptaminol} = 54} \right),$$

the two straight lines being parallel, with limits of reliance for $P=0.05$ equal to 1.417 and 5.105. If now the AD 50 of the aspirin-heptaminol association is expressed in respect of aspirin, the ratio 145/36 is then equal to 4.03 with limits of reliance for $P=0.05$, which are equal to 2.123 and 7.649.

It is therefore possible to say that, under such experimental conditions, the aspirin-heptaminol association is 2.69 times more active than aspirin alone and that furthermore the amount of aspirin required for producing the same analgesic effect is four times lower when the animals receive the aspirin-heptaminol association.

On the other hand, the total number of painful motor manifestations ('wriggles') of each animal has also been counted and for each series the mean value has been determined (with type error of the average). The averages observed in the series treated were then compared with the average observed in the 'control' group, using the Fisher-Student 't' test for homogeneous series.

| | Doses mg/kg of association | | | | |
|---|---|---|---|---|---|
| | 0 | 18.75 | 37.5 | 75.0 | 150.0 |
| Average of the number of wriggling motions | 94.9 ±9.66 | 74.9 ±9.37 | 51.2 ±6.57 | 41.7 ±8.13 | 32.1 ±6.93 |
| Percentage reduction in the number of wriggling motions | | −21.1 | −46.0 | −56.1 | −66.2 |
| Degree of significance* | | non-significant | 0.001 | 0.001 | 0.001 |
| Percentage of mice 'protected' according to Blumberg | 6.7 | 20.0 | 40.0 | 53.3 | 80.0 |

*according to the Fisher-Student 't' test for homogeneous series (two limits)

The results shown in the above-indicated Table show that the mean number of 'wriggles' induced by the intra-peritoneal injection of phenylbenzoquinone is reduced by 46% as from the dose of 37.5 mg/kg of the association ($P=0.001$), in a manner proportional to posology, to reach a difference of 66.2% at 150 mg/kg of the association, with respect to the 'control' series. The percentage of animals 'protected' in accordance with Blumberg increases proportionally to posology to reach 80% at the dose of 150 mg/kg of the association.

Clinical tests have also been carried out using the method of double crossed ignorance, as between aspirin alone and the aspirin-heptaminol association.

In these tests, the association occurred in the form of compressed tablets dosed at 350 mg of micro-encapsulated acetylsalicylic acid and 187 mg of heptaminol hydrochloride corresponding to 150 mg of base heptaminol, corresponding to the formula:

| Active principle: | MICRO-ENCAPSULATED ASPIRIN | |
|---|---|---|
| | Expressed as pure substance | 300 mg |
| | HEPTAMINOL HYDROCHLORIDE | |
| | Expressed as base | 150 mg |
| Excipients: | Methylcellulose 1500 cps, | |

-continued

| | |
|---|---|
| levilite, microcrystalline cellulose (Avicel PH 102), sodium saccharinate, powdered stearic acid, q.s.p. | 680 mg |

The aspirin occurred in the form of compressed tablets dosed at 300 mg of micro-encapsulated acetylsalicylic acid which is identical in appearance to the association,

| | | |
|---|---|---|
| Active principle: | MICROENCAPSULATED ASPIRIN Expressed as pure product | 300 mg |
| Excipients | Mannitol, microcrystalline cellulose (Avicel PH 102), methylcellulose 1500 cps, silica (levilite), sodium saccharinate, stearic acid, q.s.p. | 680 mg |

These tests were carried out on patients suffering from chronic rheumatic algias and consisted of a comparison of a therapeutic effect, and clinical and biological tolerance of the aspirin-heptaminol association, with aspirin alone.

At the conclusion of these tests, statistical analysis of the clinical results made it possible to arrive at the following conclusions:

1. The two substances, aspirin alone and association, have a statistically significant activity on pain, with a superiority in respect of action of the association ($p<0.02$).

2. There is no significant difference between the clinical and biological tolerance of the association and aspirin alone.

Clinically it is therefore possible to affirm that the association markedly improves the qualities of aspirin without increasing the disadvantages thereof.

It follows from the foregoing that the effect of aspirin is amply enhanced in the aspirin-heptaminol association.

It was also shown that the effect of heptaminol was increased in the aspirin-heptaminol association, in respect of platelet anti-aggregation, in particular in the event of venous embolisms.

For this purpose, experiments were performed 'in vivo' on anaesthetised rabbits in which an opening in the skull is made at the location of the parietal bone. The dura mater which is thus exposed and delicately raised is incised in the form of a cross. Throughout the experiment, the field of operation is covered with a film of physiological serum (9% NaCl aqueous solution) at a temperature of 37° C. The head of the animal is held in a horizontal position in a restraining apparatus and observation of the pial circulation is effected by means of a Wild binocular magnifier with an enlargement factor of 60.

The formation of venous thrombi is caused by the direct application of sodium lactate to the surface of the cortex; the contact time is set at 1 minute 30 seconds; the lactate is then drawn off by suction and the field of operation is rinsed with physiological serum.

The pial veins which can be observed after opening of the dura mater were divided up according to their diameter so that they can be more easily classified in a number of categories: veins of order I (those in which the diameter is the largest), veins of order II, veins of order III and veinlets. Veins of order I, which number only one or two per field of operation, were not taken into consideration; the veinlets which are too fine to permit discriminative observation with an enlargement factor of 60 were also eliminated from the judgment criteria. Depending on the animals, the veins of order II are 4 to 10 in number in the operating field observed; while veins of order III number from 10 to 30, according to the cases.

After application of sodium lactate, the period elapsing before the first thrombus appears in veins of order II and III is noted.

Then, 15 and 30 minutes respectively after application of sodium lactate, the state of embolisation of the pial venous vascularisation is noted, with, for each category of vessels, a subdivision into 'intact' veins and 'pathological' veins, in which there appear embolisms of platelet thrombi.

So as to have comparative results, three series of experiment were carried out:

(a) Control series

The topical application of sodium lactate to the surface of the cortex in ten vascular fields makes it possible 15 minutes later to observe the embolisation of 35.4% of the veins of order II, of substantial size, and embolisation of 45.3% thereof at the 30th minute. With regard to veins of smaller diameter (veins III), the presence of platelet thrombi is recorded in 67.8% of the cases fifteen minutes after application of lactate and in 70.7% of cases at the thirtieth minute.

(b) 'Heptaminol' series

The preventative oral administration of heptaminol for three consecutive days does not change the magnitude of the embolisation of veins of order II, of substantial size. Even when a strong dose is used (50 and even 12.5 mg/kg), there is observed a recrudescence in the number of veins in which platelet aggregates are counted, after application of the lactate.

With regard to veins of smaller diameter (veins of order III), heptaminol has a protective effect; the most marked reduction in the percentage of veins III which suffer from embolism is observed in the series treated with 6.25 mg/kg and 3.125 mg/kg of heptaminol.

(c) Aspirin+Heptaminol series

The association of aspirin with heptaminol increases the anti-platelet aggregation capability of the latter. Whereas heptaminol alone does not have any activity with regard to veins of order II, the aspirin-heptaminol association, irrespective of the dosage, substantially reduces embolisation of the pial veins; the maximum and statistically significant reduction in the number of veins 'affected' is achieved in the series 'aspirin 12.5 mg/kg-heptaminol 6.25 mg/kg' ($P=0.005$ at the 30th minute).

With regard to the finer veins of order III, a similar phenomenon is found. The addition of aspirin increases the strength of the protective capability of heptaminol with regard to the appearance of platelet aggregates in the pial veins of small diameter; the maximum therapeutic effect in this case also seems to be attained when using the association of aspirin (12.5 mg/kg)+heptaminol (6.25 mg/kg).

It will be seen from the foregoing that the platelet anti-aggregating effect of heptaminol is enhanced in the aspirin-heptaminol association.

Other tests were performed, showing the properties of that association.

Thus, the association does not change the cortical electrogenesis of the alert rabbit; it is therefore not possible to attribute to that association, central stimulating actions which evoke an amphetamine action, the therapeutic interest of which could be disputed.

In addition, toxicological evaluation of the aspirin-heptaminol association only reveals the known irritating effects of aspirin at high levels of dosage, on the mucous membrane of the digestive tract. This expert evaluation was conducted orally, in dogs and in rats, for three months; the addition of heptaminol to aspirin does not increase the known irritating effect of the latter.

As regards acute toxicity, the DL 50 was determined in mice and rats using the PROBIT method, the results are as follows:

in mice:

|  | LD 50 (g/kg) |
| --- | --- |
| Aspirin | 1.49 |
| Heptaminol hydrochloride | 3.97 |
| association* | 2.39 |

*2.39 g of association corresponds to 1054 mg of aspirin and 527 mg of heptaminol hydrochloride.

The toxicity of the association results simply from the addition without potentialisation of the toxicity of the two constituents.

- in rats:

|  | LD 50 (g/kg) |
| --- | --- |
| Aspirin | 1.87 |
| Heptaminol hydrochloride | 9.08 |
| association* | 6.99 |

*6.99 g of association corresponds to 3.083 g of aspirin and 1.541 g of heptaminol hydrochloride.

The toxicity of the association is slightly less than the sum of the toxicities (inhibition) of the two constituents.

As regards the proportion of aspirin and heptaminol in the association, the above-indicated ratio of $\frac{2}{3}$-$\frac{1}{3}$ was preferred.

Moreover, it may be found interesting for aspirin to be isolated from heptaminol so as to avoid possible deacetylation of aspirin; for this purpose, the excipient will comprise a substance permitting 'isolation' of the two main constituents. The micro-encapsulation of aspirin is one of the ways of producing such isolation.

I claim:

1. A medicament comprising an association of aspirin and heptaminol wherein the ratio of aspirin to heptaminol of two parts by weight to one part by weight.

2. A medicament according to claim 1 characterised in that heptaminol is in the form of its hydrochloride.

3. A medicament according to claim 1 characterised in that the aspirin and the heptaminol are isolated from each other.

4. A medicament according to claim 3 characterised in that the aspirin is micro-encapsulated.

5. A pharmaceutical composition according to claim 1 characterised in that it is in the form of compressed tablets comprising 300 mg of pure aspirin, 150 mg of heptaminol hydrochloride expressed as base, and excipients in a sufficient quantity for 680 mg.

6. The method of enhancing the analgesic effect of aspirin by subjects in need of same which comprises the co-administration to said subjects of heptaminol with aspirin in the ratio of one part by weight to two parts by weight.

* * * * *